United States Patent
Boffa et al.

(10) Patent No.: US 9,719,944 B2
(45) Date of Patent: Aug. 1, 2017

(54) METHOD AND APPARATUS FOR CONTROLLING TYRES IN A TYRE PRODUCTION LINE

(71) Applicant: PIRELLI TYRE S.P.A., Milan (IT)

(72) Inventors: Vincenzo Boffa, Milan (IT); Valeriano Ballardini, Imola (IT); Gabriele Pece, Milan (IT)

(73) Assignee: PIRELLI TYRE S.P.A., Milan (IT)

( * ) Notice: Subject to any disclaimer, the term of this patent is extended or adjusted under 35 U.S.C. 154(b) by 0 days.

(21) Appl. No.: 14/902,464

(22) PCT Filed: Jul. 7, 2014

(86) PCT No.: PCT/IB2014/062912
§ 371 (c)(1),
(2) Date: Dec. 31, 2015

(87) PCT Pub. No.: WO2015/004587
PCT Pub. Date: Jan. 15, 2015

(65) Prior Publication Data
US 2016/0377556 A1 Dec. 29, 2016

(30) Foreign Application Priority Data
Jul. 10, 2013 (IT) .............................. MI2013A1157

(51) Int. Cl.
*G01M 17/02* (2006.01)
*G01N 21/954* (2006.01)
(Continued)

(52) U.S. Cl.
CPC ........ *G01N 21/954* (2013.01); *G01M 17/027* (2013.01); *G01N 21/8851* (2013.01);
(Continued)

(58) Field of Classification Search
CPC .......................... G01M 17/027; G01N 21/8803
See application file for complete search history.

(56) References Cited

U.S. PATENT DOCUMENTS

| 5,616,839 A | 4/1997 | Chen et al. |
| 8,011,235 B2 * | 9/2011 | Berry .................... G01M 17/02 73/146 |

(Continued)

FOREIGN PATENT DOCUMENTS

| EP | 0 785 421 | 7/1997 |
| EP | 201410476 | 1/2010 |

(Continued)

OTHER PUBLICATIONS

Notice of Reasons for Rejection issued Jul. 20, 2016 by the Japan Patent Office in corresponding Application No. JP 2015-563020 (4 pages).

(Continued)

*Primary Examiner* — Rebecca C Bryant
(74) *Attorney, Agent, or Firm* — Finnegan, Henderson, Farabow, Garrett & Dunner, L.L.P.

(57) ABSTRACT

A method, and related apparatus, for controlling tyres in a production line, includes: predisposing a tyre to be controlled; elastically deforming a lateral wall portion of the tyre by imparting a compression force on an outer contact surface of the lateral wall portion, the compression force having axial direction and sense directed toward the middle line plane; illuminating an inner and/or outer surface of the lateral wall portion and detecting an image of the illuminated surface; generating a control signal representative of the detected image; and analyzing the control signal in order to detect the possible presence of flaws on the lateral wall portion.

36 Claims, 7 Drawing Sheets

(51) Int. Cl.
*G01N 21/95* (2006.01)
*G01N 21/952* (2006.01)
*G01N 21/88* (2006.01)
*G01N 21/17* (2006.01)

(52) U.S. Cl.
CPC ........... *G01N 21/95* (2013.01); *G01N 21/952* (2013.01); *G01N 21/17* (2013.01); *G01N 2021/8887* (2013.01)

(56) References Cited

U.S. PATENT DOCUMENTS

| | | |
|---|---|---|
| 2004/0212795 A1 | 10/2004 | Steinbichler et al. |
| 2008/0202229 A1 | 8/2008 | Maehner et al. |
| 2010/0013913 A1* | 1/2010 | Vignoli ............... B60C 25/0554 348/61 |
| 2013/0128029 A1 | 5/2013 | Leobal et al. |

FOREIGN PATENT DOCUMENTS

| | | |
|---|---|---|
| JP | 2008-190981 A | 8/2008 |
| JP | 2008-203258 A | 9/2008 |
| WO | WO 01/81886 | 11/2001 |

OTHER PUBLICATIONS

English-language translation of Notice of Reasons for Rejection issued Jul. 20, 2016 by the Japan Patent Office in corresponding Application No. JP 2015-563020 (4 pages).
International Search Report from the European Patent Office for International Application No. PCT/IB2014/062912, mailing date Sep. 3, 2014.
Written Opinion of the International Searching Authority from the European Patent Office for International Application No. PCT/IB2014/062912, mailing date Sep. 3, 2014.

* cited by examiner

METHOD AND APPARATUS FOR CONTROLLING TYRES IN A TYRE PRODUCTION LINE

CROSS REFERENCE TO RELATED APPLICATIONS

This application is a national phase application based on PCT/IB2014/062912, filed Jul. 7, 2014, and claims the priority of Italian Patent Application No. MI2013A001157, filed Jul. 10, 2013, the content of both applications being incorporated herein by reference.

BACKGROUND OF THE INVENTION

Field of the Invention

The present invention relates to a method and an apparatus for controlling tyres in a tyre production line, in particular a method and an apparatus for controlling the possible presence of flaws on or in proximity to the surface of a tyre, more particularly on or in proximity to the inner and/or outer surface of the lateral walls of a tyre.

Description of the Related Art

By "tyre" it is intended the finished tyre, i.e. after the steps of moulding and vulcanisation subsequent to the building step.

Typically, a tyre has a substantially toroidal structure around a rotation axis thereof during operation, and has an axial middle line plane orthogonal to the rotation axis, said plane being typically a plane with (substantial) geometric symmetry (e.g. ignoring possible minor asymmetries, such as the design of the tread and/or the internal structure).

Two portions of the tyre are defined herein: the crown and the lateral walls. The crown comprises the tread band, the belt and the corresponding carcass structure portion, which is radially inner with respect to the former two.

By "lateral wall" it is intended one of the two portions of the tyre that are mutually facing and are radially extended on opposite sides of the crown up to the beads, i.e. up to the two radially inner end edges of the tyre, with circular extension substantially orthogonal to the rotation axis; each of said beads being intended to be coupled with a respective mounting rim. Each lateral wall thus comprises a corresponding carcass structure portion, and in axially outer position with respect thereto, a portion made of suitable elastomeric material, generally termed 'sidewall'.

Typically, the carcass structure comprises at least one carcass ply having respectively opposite terminal flaps engaged with respective reinforcement annular structures, generally termed "bead cores", integrated in the zones identified above with the term beads. In the tyres of "tubeless" type, the carcass ply is internally covered by a layer of elastomeric material, preferably with butyl base, usually termed "liner" having optimal characteristics of impermeability to air and being extended from one bead to the other.

Also the so-called "shoulder" is intended entirely comprised in the structure of a lateral wall; such shoulder is the portion of the tyre connecting the crown and the radially more internal portion of the lateral wall (in other words, the two shoulders correspond to the two radially and axially outer circular 'edges' of the tyre). The shoulder has circular extension substantially orthogonal to the rotation axis.

By homologous portions of the tyre, it is intended portions of the same component having the same geometry. For example, homologous portions are the different angular portions of the axially outer part of a lateral wall, the angular portions of surfaces of the shoulder in their circumferential extension, the corresponding liner portions inside channels or ribs determined by the expansion bladder of the mould during moulding and vulcanisation, etcetera.

By component of the tyre it is intended any one element that performs a function or a portion thereof.

By "radius of curvature" it is intended the local radius of curvature of the surface of an element of the tyre on any one radial section plane, i.e. comprising said rotation axis (given that the radial section of the tyre typically does not vary over the entire tyre).

By outer or inner surface of the tyre, it is respectively intended the surface that remains visible after the coupling of the tyre with its mounting rim and the surface no longer visible after said coupling.

The terms 'optical', 'light' and the like make reference to an electromagnetic radiation used that has at least one portion of the spectrum falling within an enlarged area of the optical band, and not necessarily strictly falling within the optical band (i.e. 400 nm-700 nm), for example such enlarged area of the optical band may range from ultraviolet to infrared (e.g. wavelength comprised between approximately 100 nm and approximately 1 μm).

By "cycle time" within a production line comprising at least one work station, preferably a plurality of work stations, and inserted in a plant for the production of tyres, it is intended, in operating conditions, the maximum transit time for a tyre being processed to cross a work station where at least a portion of a component of the tyre itself is built. For example, the cycle time can be comprised between approximately 20 and approximately 120 seconds.

In the field of the processes of production and building of tyres for vehicle wheels, the need was perceived to execute quality controls on the obtained products, with the object of preventing defective tyres from being placed on the market, and/or to progressively adjust the apparatuses and the machinery employed, in a manner so as to improve and optimise the execution of the operations performed in the production process.

Such quality controls for example include those executed by human operators who dedicate a pre-established time, e.g. comprised between 30 s and 60 s, to a visual and tactile examination of the tyre; if, in light of one's own experience and sensitivity, the operator should suspect that the tyre does not respect certain quality standards, the tyre itself is subjected to further controls, through a more detailed human control and/or through suitable equipment, for the purpose of evaluating possible structural and/or qualitative flaws in depth.

The document US 2004/0212795 describes a method for measuring the contour and/or the deformation of an object, in particular of a tyre. The object is illuminated by a light emitted by a radiation source and in particular consists of coherent or partially coherent light, especially laser light. The light reflected by the object is received by a camera with an image sensor.

The document EP0785421 describes a method for detecting anomalies in a deformable object, by means of the observation of the dynamic changes in the deformable object using light reconstruction techniques. For example, when the pressure in an object made of reinforced rubber is varied, the weakest portions of the object expand more than the areas surrounding the object. These variations can be detected, recorded and analysed.

In the field of controls on tyres, the Applicant has addressed the problem of detecting the possible presence of flaws on or in proximity to the inner and/or outer surface of the lateral walls. The flaws sought can for example be irregularities on the surface of a tyre (non-vulcanised compound, form alterations, etc.), structural non-uniformities, presence of foreign bodies on the surface. Among the structural non-uniformities, the so-called "shifting in the carcass" is particularly critical; this is a rare flaw that can also be very dangerous, generated in the region of interface between two portions of the tyre having different chemical-physical characteristics (e.g. different compounds). Such flaws present themselves as small cuts (typically with longitudinal extension, i.e. which follows the circular extension of the tyre) characterised by perfectly mating flaps (between which there is no removal or lack of material); this characteristic makes the flaws particularly hard to identify. The shifting in the carcass can also affect structures of the carcass placed in proximity to the surface of the tyre, for example in proximity to the inner surface, below the liner layer that is typically present. In such case, typically the liner itself is involved in the shifting, it too having a tear with the shifting in the carcass and hence making the identification through optical inspection possible.

SUMMARY OF THE INVENTION

The Applicant has observed that in order for the control to be employed "in line production" within a plant for the production of tyres, it is necessary that the control itself is executed in reduced times, less than or corresponding with the aforesaid cycle time, and with limited costs.

The Applicant has realised that the methods for controlling tyres with optical acquisition of the images, described in US 2004/0212795 and/or EP0785421, are quite costly and/or time consuming, hence substantially adapted to being executed outside the production line, within a production cycle.

More precisely, the Applicant has verified that the optical control method described in the abovementioned document EP0785421 provides that the tyre is mounted on the rim, inflated and then subjected to mechanical stress, for example by creating a vacuum in the environment around the tyre, or by using acoustical vibrations, or by using a conventional machine for controlling the RFV ("Radial Force Variation").

Analogously, the method described in US 2004/0212795 provides that the tyre is subjected to various states of deformation, from whose corresponding images an average value is subsequently obtained. The deformation can be imparted by varying the ambient pressure or the temperature of the tyre.

Both documents further provide for the use of laser light and interferometric techniques, with all the disadvantages deriving from the complexity of such techniques. In addition, the Applicant has verified that, without considerable mechanical stress, the optical methods are unable to detect some flaw types, as is better specified hereinbelow.

The Applicant has in fact realised that the abovementioned optical control methods and the apparatuses do not ensure the desired accuracy and/or sensitivity in detecting possible flaws on or in proximity to the inner and/or outer surface of the lateral walls of a tyre, including shifting in the carcass.

More precisely, the optical inspection method described in US 2004/0212795 is not sufficiently reliable in detecting shifting in the carcass, since the flaps thereof tend to remain mating.

Finally, the Applicant has observed that the lateral wall of a tyre (in particular for motor vehicles) is generally characterised by a radius of curvature smaller than that of the crown (which is usually substantially flat or slightly convex) and that the shoulder is typically characterised by an internal radius of curvature smaller than the internal radius of curvature of the crown and of the rest of the lateral wall.

The Applicant has therefore addressed the problem of designing a method and an apparatus for controlling tyres based on the optical acquisition of images for the recognition of at least some flaws, in particular those in surface or near-surface zones of the lateral walls; such method and apparatus being adapted to be inserted in-line within a tyre production line of a production plant, i.e. with operating times less than or equal to a cycle time, reduced costs, reliable with regard to the obtained result, easily automatable, and in addition with a high degree of sensitivity in detecting flaws (i.e. capacity to detect even small flaws, or those that in any case are hard to detect).

The Applicant has verified that in any optical image acquisition system, the depth of field, to which an optimal focusing corresponds, decreases with the increase of the diaphragm aperture and a correct exposure requires exposure times that decrease with the increase of the diaphragm aperture and/or light intensity. The Applicant has observed that if the depth of field is limited, the convex surfaces such as those of the lateral walls may not completely fall within the available depth of field, and consequently parts of the acquired image risk being out of focus. The Applicant has then observed that the illumination, given the same light source, is affected by the geometry of the illuminated object: on non-flat surfaces, such as those of the lateral wall of the tyre, it is difficult to obtain uniform illumination over the entire surface and it is necessary to find a situation of compromise between the different zones, in order to minimise the overexposed and/or underexposed zones. Such difficulty is accentuated in illuminating the inner surface of the lateral wall for controlling the carcass.

The Applicant has found that by suitably deforming a portion of lateral wall of a tyre to be controlled, it is possible to flatten the surface of at least one sub-portion of the deformed portion, thus increasing the depth of field and improving—making more uniform—the illumination conditions for the detection of images. In such a manner, it is possible to obtain an advantageous compromise between the exposure time (which determines the diaphragm aperture and hence the depth of field), the extension of the portion subjected to control for every single image (which increases with the increase of the depth of field), and the quality (focusing) of the image itself.

The Applicant has also found that by suitably deforming a portion of lateral wall of a tyre to be controlled, it is possible to decrease the external radius of curvature of a (further) sub-portion of the deformed portion, thus further underlining possible flaws, in particular the shifting in the carcass and other cuts or holes, since the accentuation of the normal external convexity tends to 'open' the flaps or contours of such flaws, making them easier to identify in the subsequent image processing. Such effect can also be obtained on the inner, concave surface of the deformed sub-portion via flattening. The detected images therefore have high quality and/or contain information of such a quantity and quality to allow a subsequent automatic processing thereof, for the purpose of detecting possible existing flaws, rendering the algorithms for the automatic identification of flaws used for such purpose highly effective.

More precisely according to a first aspect, the invention relates to a method for controlling tyres in a tyre production line.

Preferably it is provided to predispose a tyre to be controlled, the tyre having a rotation axis and a middle line plane orthogonal to the rotation axis.

Preferably it is provided to elastically deform a portion of a lateral wall of said tyre by imparting, through physical contact, a force of compression on an outer contact surface belonging to said lateral wall portion, said compression force having at least one component parallel to the rotation axis and sense directed towards the middle line plane.

Preferably it is provided to illuminate, with a light radiation, a surface of said lateral wall portion and detect an image of said illuminated surface.

Preferably it is provided to generate at least one control signal representative of the detected image.

Preferably it is provided to analyse said at least one control signal in order to detect the possible presence of flaws on the lateral wall portion.

In accordance with a second aspect, the invention relates to an apparatus for controlling tyres in a tyre production line.

Preferably a movement member is comprised, having a support adapted to rotate the tyre around a rotation axis thereof.

Preferably a deformation system is comprised, configured for imparting, through physical contact, a compression force on an outer contact surface belonging to a portion of a lateral wall of said tyre, when the latter is supported by the support, in order to elastically deform said lateral wall portion, said compression force having at least one component parallel to the rotation axis and sense directed towards the middle line plane.

Preferably a source is comprised, adapted to emit a light radiation for illuminating a surface of said lateral wall portion and a detection system is comprised adapted to detect an image of said surface, and to generate at least one control signal representative of the detected image.

Preferably a processing unit is comprised, configured for the following functions:

receiving said at least one control signal from the detection system;

analysing said at least one control signal in order to detect the possible presence of flaws.

The Applicant deems that for the purpose of detecting flaws of a portion of a lateral wall of a tyre through acquisition and processing of optical images, it has proven to be particularly advantageous to deform said lateral wall portion by imparting, by physical contact on an outer contact surface belonging to the lateral wall portion, a compression force having at least one component parallel to the rotation axis and sense directed towards the middle line plane; in such a manner, it is possible to flatten the surface of at least one sub-portion of the deformed portion (increasing the radius of curvature thereof at at least said sub-portion). In addition or as an alternative, according to the spatial relation between the outer contact surface and the controlled sub-lateral wall portion, it is possible to decrease the external radius of curvature of at least one (further) sub-portion of the deformed portion. The result is a control of the lateral wall of the tyre through acquisition and processing of optical images executed in times less than or equal to the cycle time of a production line, and with high quality of the acquired image and information: the control of the tyres is thus fast, reliable and sensitive.

The present invention, in at least one of the aforesaid aspects, can also have one or more of the preferred characteristics that are described hereinbelow.

Preferably said analysis comprises at least the comparison of said at least one control signal with at least one corresponding reference signal.

Preferably, an alarm signal is generated following said comparison, if said control signal differs from said reference signal by more than a predefined threshold level.

Preferably the reference signal is generated by previously controlling a model tyre with the method of the present invention.

Preferably the reference signal is generated during the control of said tyre by illuminating homologous portions of the portion of said tyre subjected to control and generating said reference signal as the average of the signals obtained from each image of each homologous portion.

Preferably the reference signal is generated during the control of said tyre by means of the average of the control signals obtained on n homologous portions preceding the elastically deformed portion, wherein n is greater than or equal to one.

The Applicant deems that the generation and the use of a reference signal for detecting flaws through suitable algorithms executed by a processing unit on said control signal is particularly effective, fast, reliable and sensitive.

Preferably a bead of the tyre to be controlled is locked. Preferably the support for the tyre is configured for locking a bead. In such a manner, the tyre is not accidentally moved when subjected to the compression force.

Preferably the pressure inside the tyre to be controlled is equal to the outside pressure.

Preferably one bead of the tyre to be controlled remains free. In such a manner, the aforesaid deformation is allowed, in particular of the radially more internal lateral wall portions, i.e. closer to the axis, and in addition the access to the tyre interior is allowed.

Preferably it is provided to elastically deform said lateral wall portion, in order to flatten the surface (inner and/or outer) of at least one sub-portion of the deformed lateral wall portion.

The outer contact surface more preferably belongs to a shoulder or to a radially central portion of the lateral wall.

Preferably, the flattened inner surface of said sub-portion is illuminated in order to detect the image thereof, said inner surface being situated on the side opposite said outer contact surface. Preferably, the flattened outer surface of said sub-portion is illuminated in order to detect the image thereof, said illuminated outer surface being situated in a position adjacent to said outer contact surface, with reference to the circular extension direction of the lateral wall.

Preferably it is provided to elastically deform said lateral wall portion in order to decrease the external radius of curvature of at least one (further) sub-portion of said lateral wall portion.

Preferably the outer surface of said at least one (further) sub-portion is illuminated, in order to detect the image thereof and said outer surface is situated in radially more external position with respect to said outer contact surface.

Preferably the outer contact surface belongs to a radially central portion of the lateral wall and said (further) sub-portion is situated at the respective buttress.

Preferably the outer contact surface is close to the bead (in general closer to the bead than to the crown) and said sub-portion belongs to a radially central portion of the lateral wall.

In such a manner, advantageously, the sub-portion that is radially more external with respect to said outer contact surface acts as a hinge of the deformation (since the crown, in this context, has a substantially rigid behaviour) and hence undergoes a decrease of the external radius of curvature with respect to that without forces. Such enhancement of the normal external convexity opens the cuts possibly present on the outer surface of the sub-portion.

Preferably the compression force is parallel to the rotation axis.

Preferably it is provided to deform said lateral wall portion, maintaining at least one further portion of the lateral wall non-deformed.

Preferably the compression force is such to deform said lateral wall portion in a manner such that the maximum travel, taken from among all the points of said lateral wall portion between the position without forces and the deformed position, the travel being taken along the direction of the compression force, is greater than or equal to approximately 0.5 cm.

Preferably the maximum travel is greater than or equal to 1.5 cm.

Preferably the maximum travel is less than or equal to 5 cm.

Preferably the maximum travel is less than or equal to 3 cm.

The Applicant has verified that such value intervals ensure an advantageous flattening of the surface to be controlled and/or an advantageous opening of possible cuts.

Preferably said compression force is, in modulus, greater than or equal to 40 N.

Preferably said compression force is greater than or equal to 50 N.

Preferably said compression force is less than or equal to 80 N.

Preferably said compression force is less than or equal to 70 N.

The Applicant has empirically verified that such force values are such to ensure a good compromise from among the different deformations to which the different tyre models are subjected and/or, for one same model, to which the different radial lateral wall portions are subjected. In such a manner, it is possible to design a single control of tyres that ensures the desired performances for various types or sizes of tyres.

Preferably it is provided to repeat the aforesaid actions of deforming, illuminating, detecting an image, generating and analysing a control signal in time sequence on a plurality of further portions of the lateral wall in addition to said lateral wall portion, said plurality being distributed along the circular extension of the lateral wall.

Preferably, for such purpose the tyre is rotated around the axis thereof, maintaining said compression force on the successive lateral wall portions.

Preferably said plurality of further portions of the lateral wall are continuous with each other and constitute, with said lateral wall portion, the entire lateral wall.

Preferably the compression force is maintained constant.

Preferably it is provided, subsequent to the action of elastically deforming said lateral wall portion and before detecting the image, to rotate the tyre around the axis thereof by at least half a revolution, maintaining said compression force.

Still more preferably, it is provided to rotate the tyre around the axis thereof for three revolutions, maintaining said compression force. In such a manner, advantageously, the adaptation of the tyre to the exerted force is facilitated.

Preferably it is provided to impart said compression force by pressing a cylindrical compression roller against said outer contact surface, the roller being able to freely rotate around the axis thereof.

Preferably the deformation system comprises a compression member and an actuator member adapted to move the compression member along the direction of the compression force.

Preferably the compression member comprises a framework mounted on the end of the actuator member and a cylindrical compression roller mounted on the framework in a manner such that it can freely rotate around the axis thereof.

Preferably the axis of the compression roller lies on a plane passing through the axis of the tyre and through the radial direction of the lateral wall portion subjected to deformation.

Preferably the length of the roller along the axis thereof is greater than the radial length of the lateral wall of the tyre.

Preferably the length of the roller along the axis thereof is greater or equal to approximately 5 cm.

Preferably the length of the roller along the axis thereof is less than or equal to approximately 25 cm.

Preferably the radius of the compression roller is greater or equal to approximately 1 cm.

Preferably the radius of the compression roller is less than or equal to approximately 4 cm.

The Applicant has found that such conformation and/or orientation of the compression roller confers a suitable deformation to the lateral wall portion for the purposes of the automatic flaw detection.

Preferably the framework comprises a bracket on which the compression roller is mounted rotatably free, the bracket being hinged on the remaining body of the framework in a manner such that the bracket, and the compression roller therewith, can oscillate around an oscillation axis thereof.

Preferably the oscillation axis is perpendicular to the axis of the tyre and perpendicular to the radial direction of the lateral wall portion subjected to deformation.

Preferably the oscillation axis, in rest position of the compression roller, is placed above, with reference to a vertical direction parallel to the rotation axis of the tyre, a median portion of the compression roller.

Preferably the axis of the compression roller in operation diverges from a condition of perpendicularity with the axis of the tyre within a ±60° interval.

Preferably two springs are interposed between the bracket and the remaining body of the framework on opposite sides of the oscillation axis bring forth a predetermined resistance to said oscillation.

The Applicant has advantageously found that the compression roller as described above can be adapted to the slope of the lateral wall portion on which it exerts the compression, being adapted to the consequent deformation.

Preferably the compression system comprises a radial movement member adapted to integrally move the compression member and the actuator member along the radial direction of the tyre.

Preferably the light illumination radiation is broadband. Preferably the light radiation is incoherent white light.

Preferably the detection system comprises a camera having a digital optical sensor and an optical objective with a focal axis thereof.

Preferably the camera is of linear type, aligned along the radial direction. In such a manner, it is advantageously possible to acquire the images of radial surface portions.

The detection system preferably comprises a mirror for allowing the illumination and/or detection of the image of the inner surface.

Preferably the apparatus comprises at least one robotic arm, at whose free end said detection system and said source are mounted.

Preferably the detected image of the illuminated surface is a digital image consisting of a plurality of pixels, each corresponding with a small sub-portion of surface having finite size.

Preferably it is provided to detect an image and/or generate a control signal and/or analyse the control signal, for each pixel of the digital image.

Preferably said processing unit is also configured for commanding and controlling said apparatus.

Preferably it is provided to control a plurality n of tyres in a predefined time interval.

Preferably said time interval corresponds with n times a cycle time of the production line. In such a manner, it is possible to maintain the control of each tyre in-line during the production, preventing the aforesaid control from having to be executed outside the production line.

Preferably, subsequent to the control, in the same predefined time interval it is provided to maintain k tyres in the production line, with k=<n, and send n−k tyres outside said production line, as a function of the aforesaid control signal. The Applicant deems that in this manner it is possible to obtain, in acceptable time periods and in a precise and reliable manner, a control of the surface of the tyres that can be advantageously used for controlling the quality of the tyres in a production line.

Preferably each of said n−k tyres sent outside the production line is sent to a check station for carrying out at least one further test on the same tyre. In this manner, it is possible to determine with greater accuracy the problems that each tyre has, and hence it is possible to decide in a more reliable manner if such tyre must be discarded or not.

Preferably, a tyre production line comprises at least one work station, at least one moulding and vulcanisation station, and at least one control station comprising an apparatus for controlling tyres in accordance with the apparatus of the second aspect of the present invention, in any one of its embodiments.

Preferably the tyre control station comprises a tyre overturning machine adapted to arrange the tyre on a sidewall opposite that which lies on the support.

Preferably the tyre control station comprises a pair of the apparatuses for controlling tyres in a production line according to the present invention and, interposed between the two apparatuses with reference to a production flow, said overturning machine.

BRIEF DESCRIPTION OF THE DRAWINGS

Further characteristics and advantages will be clearer from the detailed description of several exemplifying but non-limiting embodiments of a method and an apparatus for controlling tyres in a tyre production line, in accordance with the present invention. Such description will be set forth below with reference to the enclosed figures, provided only for exemplifying and hence non-limiting purposes, in which.

DETAILED DESCRIPTION OF THE INVENTION

With reference to the figures, the reference number 1 generally indicates a production line in which a control is performed, executed through the method and/or the apparatus according to the present invention. In general, the same reference number will be used for similar elements, even in the modified embodiments thereof.

Figure 1:
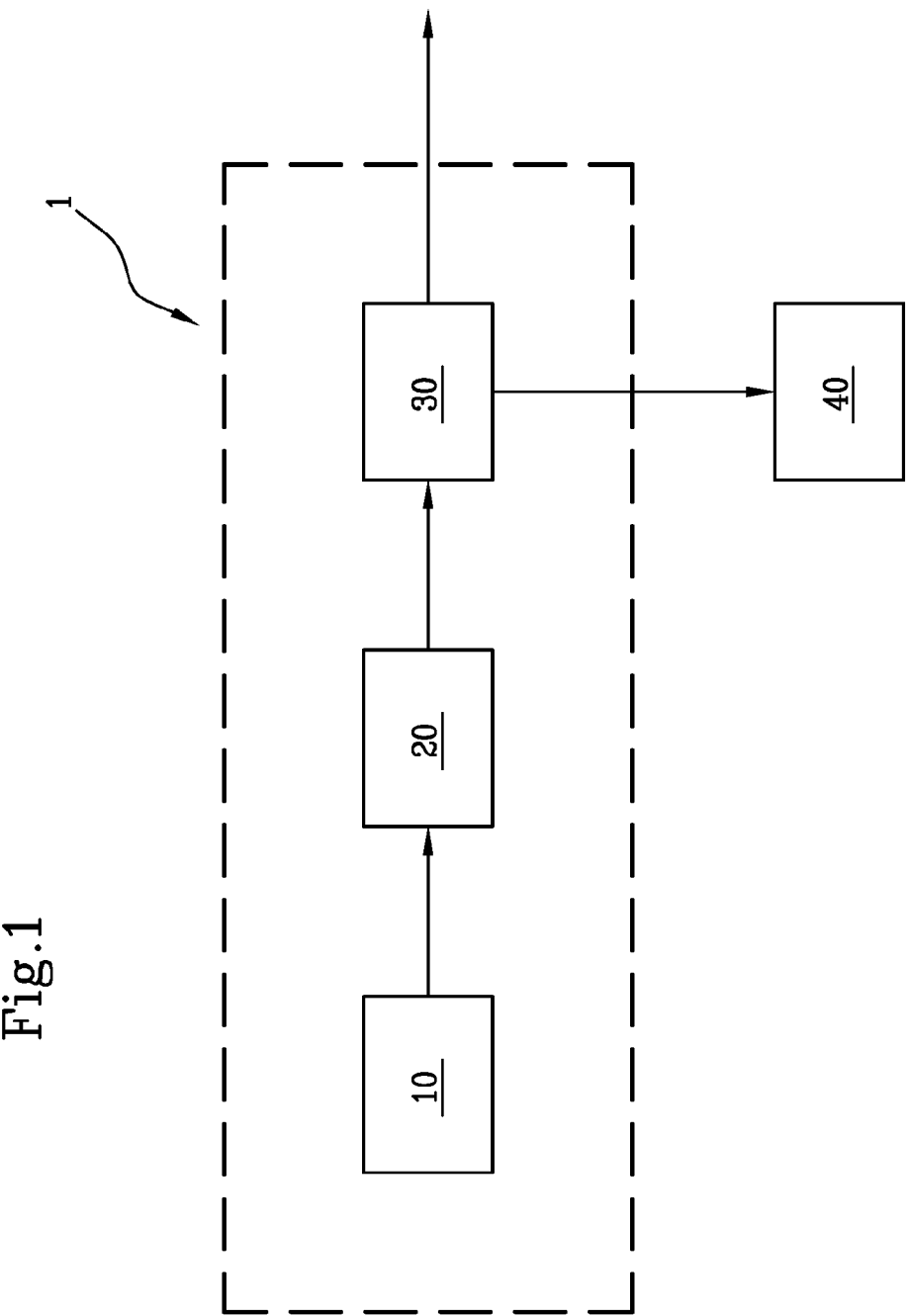
FIG. 1 shows, in functional block terms, a production line according to the present invention.

The production line 1 (indicated with the dashed line in FIG. 1) comprises at least one work station 10, at least one vulcanisation station 20 and at least one control station 30 downstream of the vulcanisation station 20 (with reference to a production flow indicated by the arrows). The production line 1 can also comprise further stations, not illustrated in detail herein.

Figure 7:
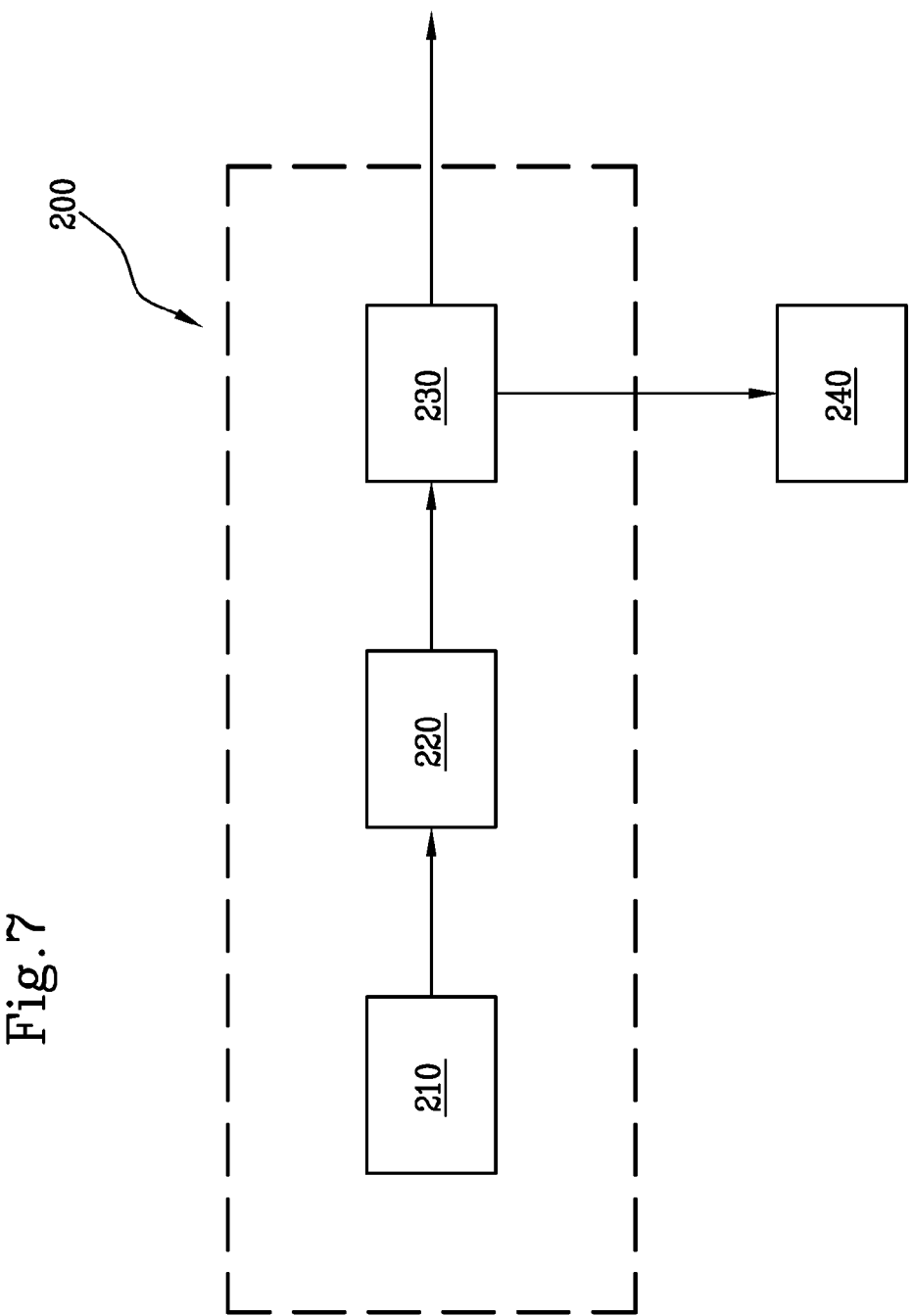
FIG. 7 shows a flow diagram, of a tyre production process in accordance with the present invention.

A flow diagram of a process 200 for producing tyres in accordance with the present invention is schematically illustrated in FIG. 7.

The process 200 comprises at least one operation 210 for building green tyres (typically carried out in the aforesaid work station 10), an operation of moulding and vulcanising 220 green tyres (typically carried out in the aforesaid vulcanisation station 20 following the building operation 210) and an operation 230 for controlling moulded and vulcanised tyres (typically carried out in the aforesaid control station 30 following the moulding and vulcanisation operation 220).

The tyre control operation 230 provides for controlling n tyres in a predefined time interval, for example equal to approximately n times a cycle time. For example, in the predefined time interval, a flow of n tyres is fed into the inlet of the control station 30.

Preferably, the n tyres will be sequentially processed, one after the other, by the same devices present in the control station 30.

The control station 30 comprises at least one apparatus 100 for controlling tyres in a production line according to the method of the present invention.

Figure 6:
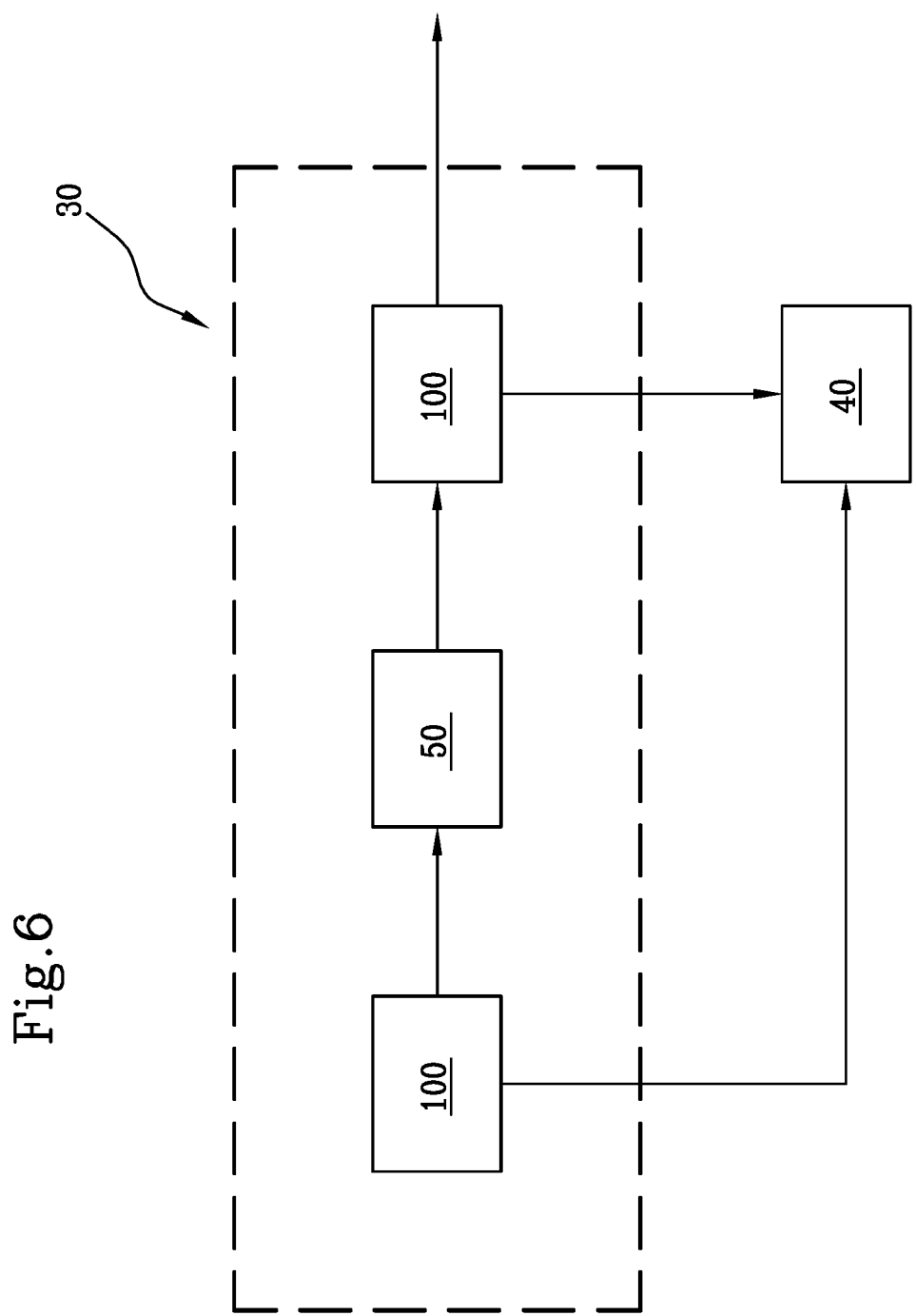
FIG. 6 shows a schematic diagram, in functional block terms, of a control station in accordance with the present invention.

As shown in FIG. 6, the tyre control station 30 can comprise a pair of the aforesaid apparatuses 100 for controlling tyres in a production line and, interposed between the two apparatuses with reference to the production flow, a tyre overturning machine 50 adapted to set the tyre on a sidewall opposite that which lies on the support of the first apparatus 100 (to the left in FIG. 6). In such a manner, it is possible to sequentially control the two lateral walls of the tyre respectively in the two apparatuses 100.

The control operation executed on each single tyre by each apparatus 100 provides for the use method according to the present invention.

As a function of the control signal generated for each tyre, the control station 30 establishes how to direct the n tyres received in inlet:

k tyres (with k<=n) are maintained in the production line (for example they are sent to further test and/or verification stations or subjected to operations of labelling, storing etc.), since they are deemed suitable;

n–k tyres are instead sent outside the production line, since they are at least preliminarily deemed unsuitable.

Preferably the maintenance of the k tyres in the production line and the sending of the n–k tyres outside the production line is executed in a time equal to the above-mentioned predefined time interval.

Preferably the n–k tyres sent outside the production line are sent to a check station 40 (outside the production line), where more in-depth analysis can be carried out aimed to verify if the tyres must be definitively discarded. The production process consequently provides for an operation (outside production line) of further verification 240 (executed in the check station 40) after the control operation, carried out only on the n–k tyres deemed unsuitable at least preliminarily. For example, the results of the aforesaid verification can be the following for each tyre: "good" tyre, tyre "good but to be reprocessed", tyre "defective to be discarded (waste)", with classification of the flaw and check in the production line.

The apparatus 100 comprises a movement member 101 for a tyre 200 having a support 102 adapted to rotate the tyre around the rotation axis 201 thereof, typically arranged according to the vertical. In the figures, the movement member 101 for the tyre is only shown relative to the support 102, since it can for example be of known type. Preferably the support for the tyre is configured for locking a bead, for example by means of suitable radially movable clamps 103.

The tyre has a substantially toroidal structure around the rotation axis 201, and has an axial middle line plane 202 (represented in section by a dashed line in FIGS. 3, 4 and 5) orthogonal to the rotation axis. The tyre is composed of the crown 203 and the lateral walls 204. In turn, the latter are each composed of a shoulder zone 205, a bead zone 206 and a radially central zone 207 interposed between shoulder and bead.

The apparatus comprises a deformation system 110 configured for imparting, through physical contact, a compression force on an outer contact surface belonging to a portion of a lateral wall of the tyre, when the latter is supported by the support, in order to elastically deform the lateral wall portion. In a preferred configuration, for example shown in the figures, the compression force (indicated by the vertical arrow in FIG. 3) is directed like the rotation axis. Nevertheless, according to the Applicant the present invention comprises the cases in which the compression force has at least one component parallel to the rotation axis. For such purpose, the Applicant deems that the desired deformation effects can be obtained for a direction of the compression force that diverges from the direction parallel to the rotation axis by not more than ±60°. The compression force also has sense directed towards the middle line plane 202.

Figure 2:
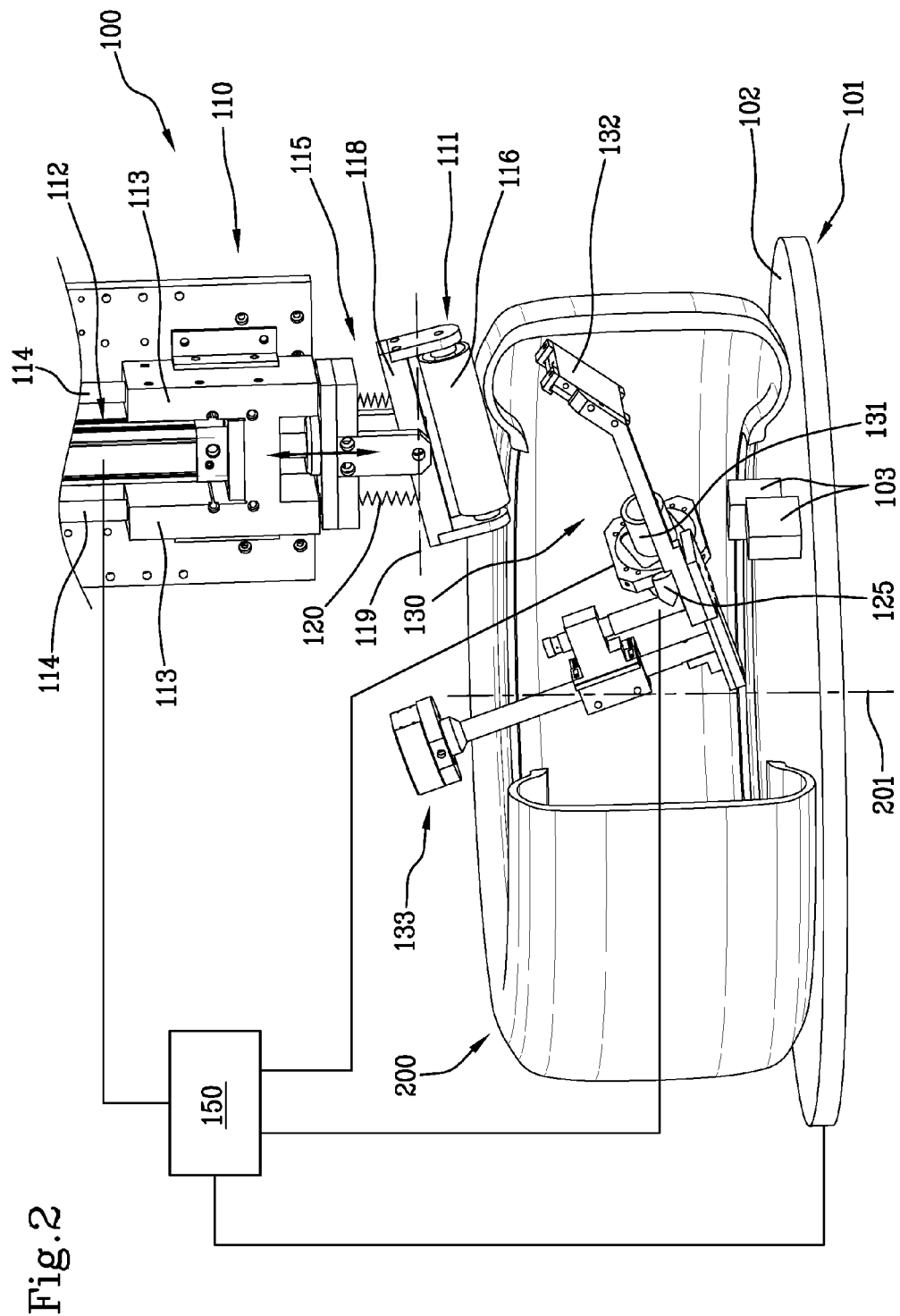
FIG. 2 shows a partial and schematic perspective view, partially in cross section and partially in terms of functional blocks, of an apparatus for controlling tyres in accordance with the present invention.

Preferably the deformation system 110 comprises a compression member 111 and an actuator member 112 adapted to move the compression member along the direction of the compression force (as indicated for example by the double arrow in FIG. 2). As an example, the actuator member 112 can be a pneumatic cylinder (as shown in the figures). For example, the deformation system 110 comprises a pair of slide guides 113 (integral with the pneumatic cylinder and arranged on opposite sides thereof) and a pair of shafts 114 slidable within the guides 113 along the direction of the compression force and integral with the compression member 111, in order to stabilise the compression member in each operating condition.

Preferably the compression member 111 comprises a framework 115 integrally mounted on the end of the piston of the pneumatic cylinder (and on the corresponding ends of the shafts 114) and a cylindrical compression roller 116 mounted on the framework in a manner such that it can freely rotate around the axis thereof 117. For example, the length of the compression roller along the axis thereof is equal to approximately 20 cm and the radius of the roller is equal to approximately 1.5 cm.

Preferably the framework 115 comprises a bracket 118 on which the compression roller is rotatably mounted, the bracket being hinged on the remaining body of the framework (the latter being rigidly integral with the pneumatic piston) in a manner such that the bracket, and the roller therewith, can oscillate around an oscillation axis 119 (indicated by a dashed line in FIG. 2).

Figure 3:
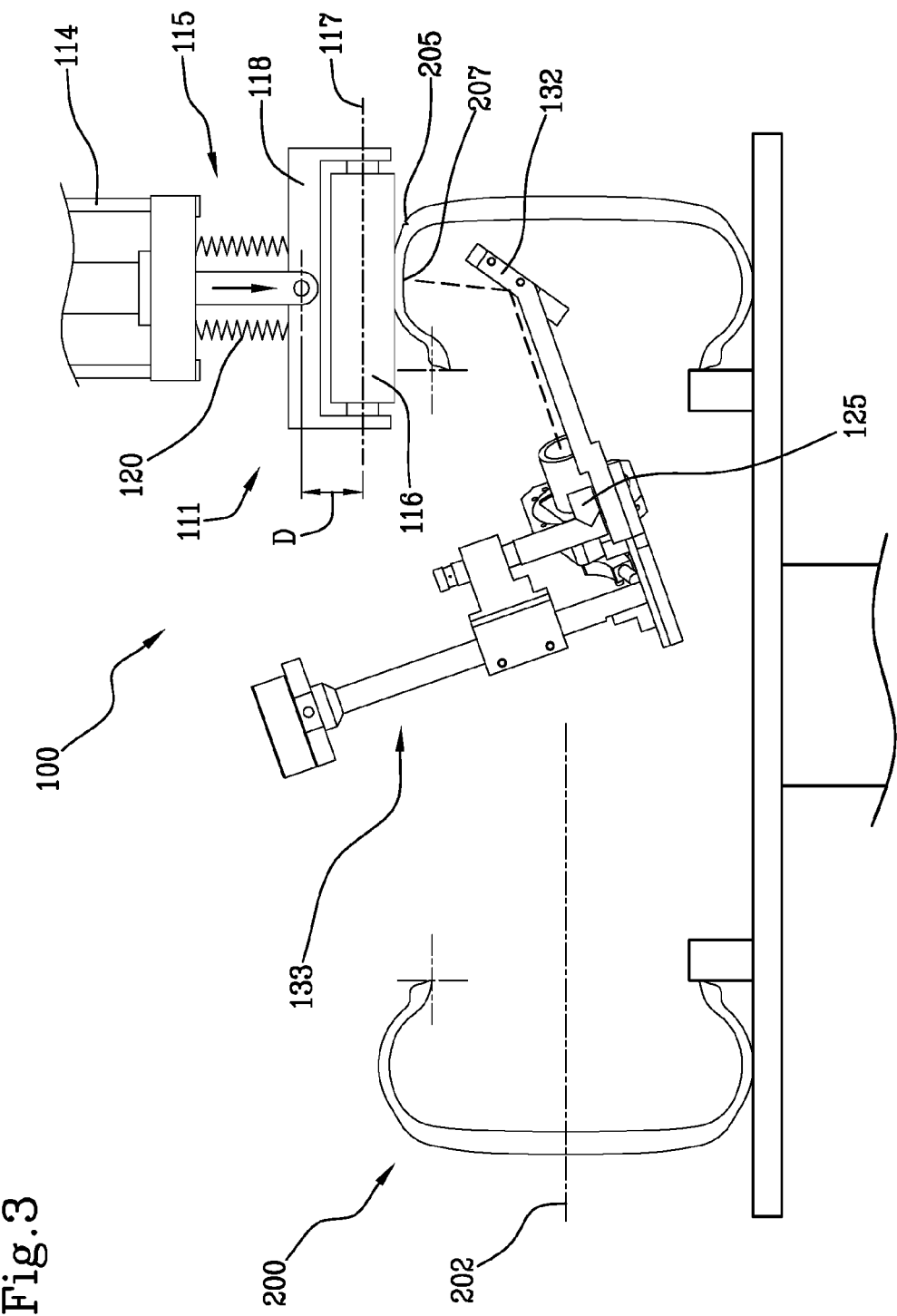
FIGS. 3, 4 and 5 show several side and partial views, partially in section, of the apparatus of FIG. 2 in different respective operative configurations according to the method of the present invention.
Figure 4:
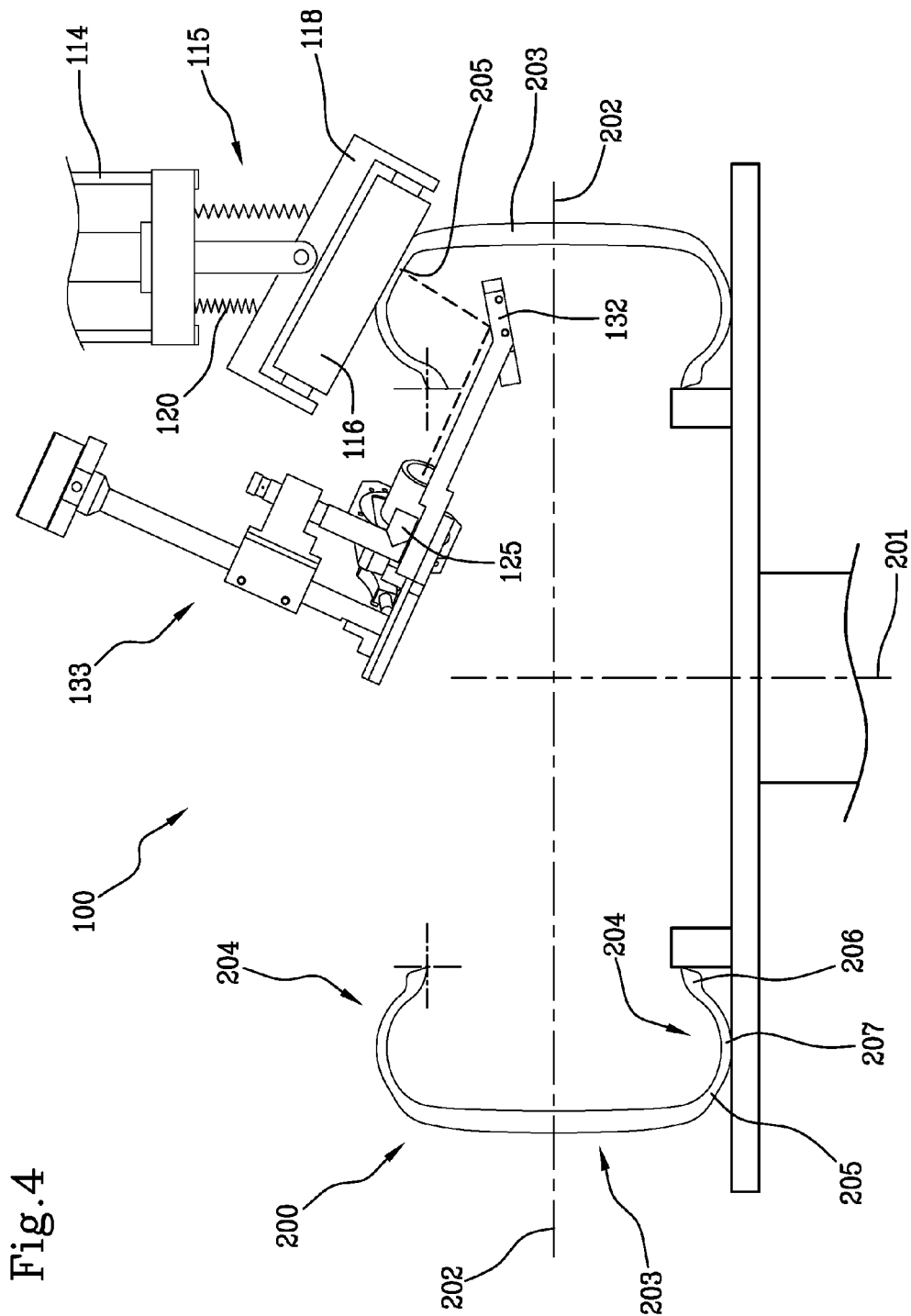

Preferably the oscillation axis 119 is perpendicular to the axis of the tyre 201 and perpendicular to the radial direction of the lateral wall portion subjected to deformation (such radial direction coinciding for example with the line 202 of FIG. 4). In FIG. 3, D represents the vertical distance of the oscillation axis from the rotation axis of the roller, in rest position thereof, i.e. without compression force.

Preferably two springs 120 are interposed between the bracket 118 and the remaining body of the framework 115 on opposite sides of the oscillation axis 119 in order to bring forth a predetermined resistance to the oscillation.

Figure 5:
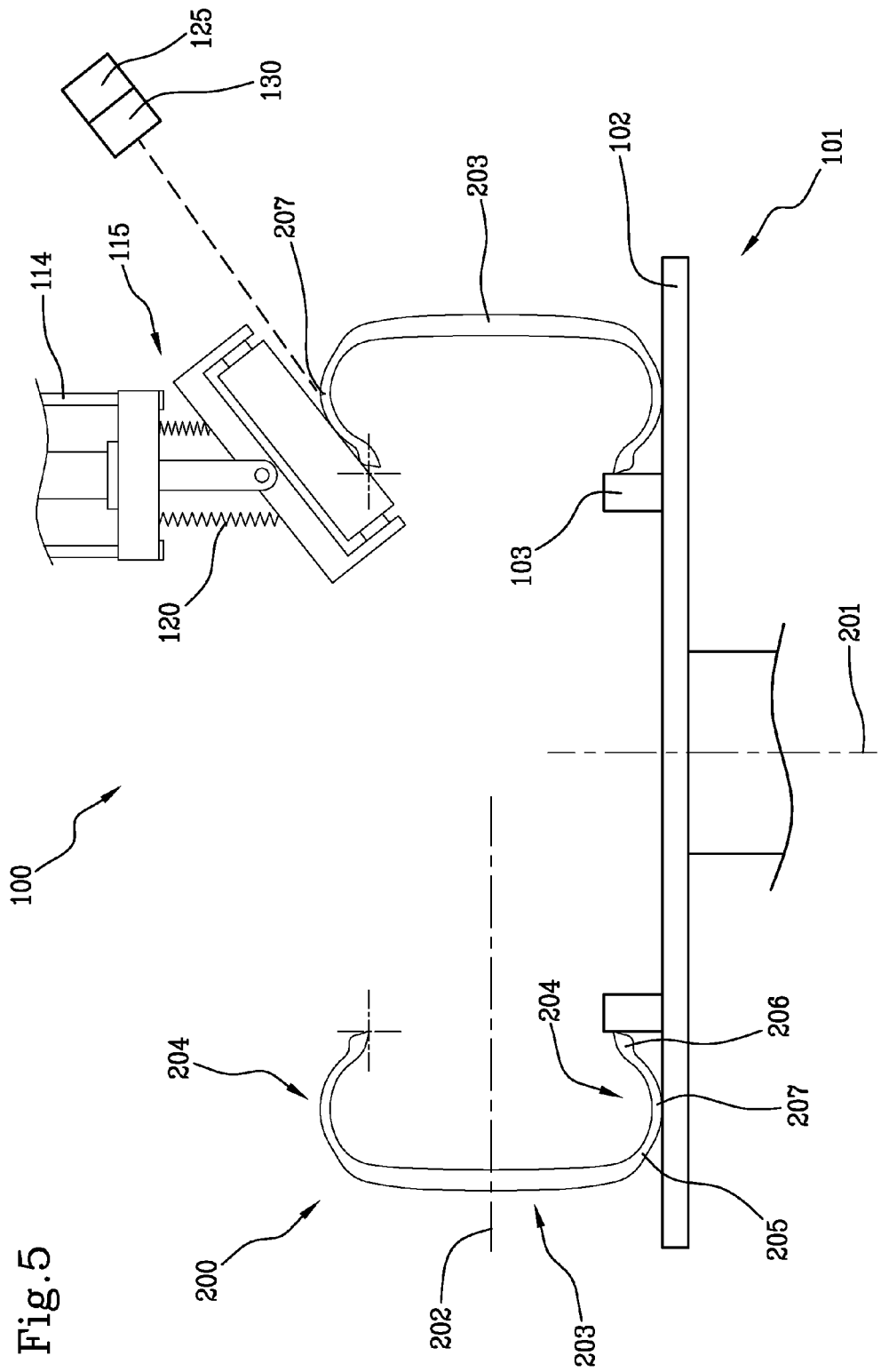

Preferably the axis 117 of the compression roller always lies on a plane passing through the axis of the tyre and through the radial direction of the lateral wall portion subjected to deformation (e.g. the lying plane of FIGS. 3, 4 and 5). Preferably the axis 117 of the compression roller, without forces, i.e. in rest position, is perpendicular to the axis of the tyre. The axis of the roller, in operation, due to the oscillation may diverge from such condition of perpendicularity with the axis of the tyre (as shown for example in FIGS. 4 and 5) within the ±60° interval.

Preferably the deformation system 110 comprises a radial movement member (not shown, for example a further pneumatic piston and a guide and block system for guiding the radial movement) adapted to integrally move the compression member and the actuator member along the radial direction of the tyre.

The apparatus 100 comprises a source 125 adapted to emit a light radiation for illuminating a inner and/or outer surface of the deformed lateral wall portion and a detection system 130 adapted to detect an image of said surface, and to generate at least one control signal representative of the detected image.

Preferably the light illumination radiation is an incoherent white light. Alternatively, the light radiation can be (coherent) light with narrow band, e.g. laser light.

Preferably the detection system 130 comprises a linear camera 131, which can be of two-dimensional (2D) or three-dimensional (3D) type, having a digital optical sensor (for example of coupled charged device or CCD type), white or black, or more typically colour, and an optical objective with a focal axis thereof (e.g. the barycentre axis of the objective lenses).

The detection system 130 preferably comprises a mirror 132 for allowing the detection of the image of the inner surface.

Preferably the apparatus comprises a robotic arm 133 at whose free end said detection system 130 and said source 125 are mounted.

The apparatus comprises a processing unit 150 configured for receiving, from the detection system 130, the control signal and for analysing the control signal in order to detect the possible presence of flaws.

Preferably the processing unit 150 is also configured for commanding and controlling the apparatus 100. For such purpose, it is operatively connected (as schematically indicated by the connection lines in FIG. 2) with the camera 131, the light source 125, the actuator member 112, the possible radial movement member and the movement member 101 for the tyre.

In operation, the apparatus 100 can control each single tyre by implementing the method of the present invention. The following description refers to a single tyre. That described can also be applied to each of the n tyres constituting the incoming flow.

In operation, a tyre 200 is abutted against the support 102 (e.g. by means of a robotic arm, not shown). Preferably the pressure inside the tyre to be controlled is equal to the outside pressure (i.e. the tyre remains deflated). Preferably the lower bead of the tyre is locked by means of the clamps 103 and the opposite or upper bead remains free (i.e. no mounting rim is utilised).

A portion of a lateral wall is elastically deformed by imparting the compression force on an outer contact surface belonging to the lateral wall portion, by pressing the aforesaid compression roller on the outer contact surface.

Preferably the entire remaining portion of the lateral wall remains non-deformed. In an alternative embodiment, one (or even multiple) further deformation system, coupled to a further light source and a further detection system, subjects the tyre to the same operations described herein, at a point of the tyre diametrically opposite the aforesaid deformed lateral wall portion. In the case of multiple deformation systems, these will be angularly equidistant from each other. In such a manner, the time of acquisition of the images is halved (or further decreased). In any case at least one further lateral wall portion remains non-deformed.

As an example, the compression force is such to deform the lateral wall portion in a manner such that the maximum travel, taken from among all the points of said lateral wall portion between the position without forces and the deformed position, the travel being taken along the direction of the compression force, is equal to 2 cm.

As an example, the compression force is equal to 60 N.

Preferably the tyre is then preliminarily rotated around the axis thereof by at least half a revolution, maintaining the compression member pressed.

Subsequently, an inner and/or outer surface of the lateral wall portion is illuminated with a light radiation and an image is detected of the illuminated surface. Preferably the image is a digital image consisting of a plurality of pixels, each corresponding to a small sub-portion of surface having finite size.

Subsequently, at least one control signal is generated, representative of the detected image.

Subsequently, the control signal is analysed in order to detect the possible presence of flaws (e.g. irregularities and/or foreign bodies on or in proximity to the surface) on the lateral wall portion.

Preferably the analysis comprises at least the comparison of the control signal with a corresponding reference signal.

Preferably an alarm signal is generated following the aforesaid comparison if the control signal differs from the reference signal by more than a predefined threshold level.

Preferably the reference signal is generated by previously controlling a model tyre.

Preferably the reference signal is generated during the control of the same tyre subjected to control, by illuminating homologous portions of the portion of tyre subjected to control and generating the reference signal as the average of the signals obtained from each image of each homologous portion.

Preferably the reference signal is generated during the control of the same tyre subjected to control by means of the average of the control signals obtained on n homologous portions preceding the elastically deformed portion, wherein n is greater than or equal to one.

Preferably the tyre is then rotated around the axis thereof, maintaining the deformation system stopped and the compression force on the subsequent lateral wall portions constant. In one embodiment, the deformation system, the source and the detection system may rotate around the axis, following the lateral wall (with the tyre stopped or even in addition to the rotation of the tyre). In such a manner, the aforesaid actions are repeated: deforming, illuminating, detecting an image, generating and analysing a control signal in time sequence on a plurality of further portions of the lateral wall in addition to the aforesaid lateral wall portion, said plurality being distributed along the circular extension of the lateral wall in a manner so as to control the entire lateral wall.

FIGS. 3, 4 and 5 show the apparatus 100 in different respective exemplifying operative configurations, each corresponding with a respective mode for executing the control method of the present invention. FIGS. 3 and 4 show examples of elastic deformation of the lateral wall portion, in order to flatten the inner and/or outer surface of at least one sub-portion of the deformed lateral wall portion. In FIG. 4, the outer contact surface belongs to a shoulder 205, while in FIG. 3 it belongs to a radially central portion 207 of the lateral wall. In FIGS. 3 and 4, the flattened inner surface of the sub-portion is exemplifyingly illuminated, in order to detect the image thereof, said flattened inner surface being situated on the side opposite the outer contact surface. In addition to or as an alternative to such illumination and image detection, in the case of the deformation shown in FIGS. 3 and 4, the flattened outer surface can be preferably illuminated (not shown); the latter surface is situated in a position adjacent to the outer contact surface, with reference to the circular extension direction of the lateral wall in the relative advancement sense between the tyre 200 and the cylindrical compression roller 116.

FIG. 5 shows an example of elastic deformation of the lateral wall portion in order to decrease the external radius of curvature of at least one sub-portion of the deformed lateral wall portion. In such case, the outer surface of the sub-portion is illuminated in order to detect the image thereof. In order to simplify the illustration, in FIG. 5 the illumination and detection system was only schematised in terms of functional blocks; in any case, it is provided outside and above the tyre. In the case of the deformation of FIG. 5, the outer contact surface is close to the free bead 206 and the controlled sub-portion belongs to a radially central portion 207 of the lateral wall.

Also the elastic deformation shown in FIG. 3 can constitute an example of elastic deformation of the lateral wall portion in order to decrease the external radius of curvature of at least one sub-portion of the deformed lateral wall portion. In such case, the outer contact surface belongs to a radially central portion 207 of the lateral wall and the controlled sub-portion is situated at the respective shoulder 205. It is observed that in FIG. 3 the illumination and detection system is shown in the position for acquiring the images of the inner surfaces (described above), while in the present case (not shown) it should be positioned outside the tyre, as schematised in FIG. 5.

In both of the latter two above-described cases, the controlled sub-portion is radially more external with respect to the outer contact surface.

The invention claimed is:

1. A method for controlling tyres in a tyre production line, comprising:
predisposing a tyre to be controlled, the tyre having a rotation axis and a middle line plane orthogonal to the rotation axis;
elastically deforming a portion of a lateral wall of said tyre by imparting, through physical contact, a force of compression on an outer contact surface belonging to said lateral wall portion, said compression force having at least one component parallel to the rotation axis and sense directed toward the middle line plane;
illuminating, with a light radiation, one surface of said lateral wall portion and detecting an image of said illuminated surface;
generating at least one control signal representative of the detected image; and
analysing said at least one control signal in order to detect a possible presence of flaws on the lateral wall portion.

2. The method as claimed in claim 1, wherein said analysis comprises at least a comparison of said at least one control signal with at least one corresponding reference signal.

3. The method as claimed in claim 2, wherein an alarm signal is generated following said comparison if said control signal differs from said reference signal by more than a predefined threshold level.

4. The method as claimed in claim 2, wherein the reference signal is generated by previously controlling a model tyre.

5. The method as claimed in claim 2, wherein the reference signal is generated during control of said tyre by illuminating portions homologous to a portion of said tyre subjected to control and generating said reference signal as an average of signals obtained from each image of each homologous portion.

6. The method as claimed in claim 2, wherein the reference signal is generated during control of said tyre by means of an average of control signals obtained on n homologous portions preceding the elastically deformed portion, wherein n is greater than or equal to one.

7. The method as claimed in claim 1, wherein a bead of the tyre to be controlled is locked.

8. The method as claimed in claim 1, wherein the pressure inside the tyre to be controlled is equal to the outside pressure, one bead of the tyre to be controlled remaining free.

9. The method as claimed in claim 1, comprising elastically deforming said lateral wall portion in order to flatten an inner and/or outer surface of at least one sub-portion of the deformed lateral wall portion.

10. The method as claimed in claim 1, wherein the outer contact surface belongs to a shoulder or to a radially central portion of the lateral wall.

11. The method as claimed in claim 9, wherein the flattened inner surface of said sub-portion is illuminated in order to detect an image thereof, said illuminated inner surface being situated on a side opposite said outer contact surface.

12. The method as claimed in claim 9, wherein the flattened outer surface of said sub-portion is illuminated in order to detect an image thereof, said illuminated outer surface being situated in a position adjacent to said outer contact surface, with reference to a circular extension direction of the lateral wall.

13. The method as claimed in claim 1, comprising elastically deforming said lateral wall portion in order to decrease an external radius of curvature of at least one sub-portion of said lateral wall portion.

14. The method as claimed in claim 13, wherein an outer surface of said at least one sub-portion is illuminated in order to detect the image thereof, and said illuminated outer surface is situated in a radially more external position with respect to said outer contact surface.

15. The method as claimed in claim 13, wherein the outer contact surface belongs to a radially central portion of the lateral wall and said sub-portion is situated at the respective shoulder.

16. The method as claimed in claim 13, wherein the outer contact surface is close to the bead and said sub-portion belongs to a radially central portion of the lateral wall.

17. The method as claimed in claim 1, wherein the compression force is parallel to the rotation axis.

18. The method as claimed in claim 1, comprising providing deforming said lateral wall portion, maintaining at least one further portion of the lateral wall non-deformed.

19. The method as claimed in claim 1, wherein the compression force is such to deform said lateral wall portion in a manner such that a maximum travel, taken from among all points of said lateral wall portion, between a position without forces and the deformed position, the travel being taken along a direction of the compression force, is greater than or equal to approximately 0.5 cm and less than or equal to approximately 5 cm.

20. The method as claimed in claim 1, wherein said compression force is, in modulus, greater than or equal to approximately 40 N and less than or equal to approximately 80 N.

21. The method as claimed in claim 1, comprising repeating the deforming, illuminating, detecting an image, generating and analysing a control signal in time sequence on a plurality of further portions of a lateral wall beside said lateral wall portion, said plurality being distributed along a circular extension of the lateral wall, wherein said plurality of further portions of the lateral wall are continuous with each other and constitute, with said lateral wall portion, an entire lateral wall.

22. The method as claimed in claim 21, wherein the compression force is maintained constant.

23. The method as claimed in claim 1, comprising, subsequent to elastically deforming said lateral wall portion and before detecting the image, rotating the tyre around an axis thereof by at least half a revolution, maintaining said compression force.

24. The method as claimed in claim 1, comprising imparting said compression force by pressing a cylindrical compression roller against said outer contact surface, the roller being able to freely rotate around an axis thereof.

25. The method as claimed in claim 1, comprising controlling a plurality n of tyres in a predefined time interval, said time interval corresponding to n times a cycle time of said production line.

26. The method as claimed in claim 25, comprising, in a same predefined time interval, maintaining k tyres in the production line, with k=<n, and sending n-k tyres outside said production line, as a function of the control signal.

27. The method as claimed in claim 26, wherein each of said n-k tyres sent outside the production line is sent to a check station for carrying out at least one further test on a same tyre.

28. An apparatus for controlling tyres in a tyre production line, comprising:
- a movement member having a support adapted to rotate the tyre around a rotation axis thereof;
- a deformation system configured for imparting, through physical contact, a compression force on an outer contact surface belonging to a portion of a lateral wall of said tyre, when said tyre is supported by the support, in order to elastically deform said lateral wall portion, said compression force having at least one component parallel to the rotation axis and sense directed toward a middle line plane of the tyre;
- a source adapted to emit a light radiation for illuminating a surface of said lateral wall portion and a detection system adapted to detect an image of said surface, and to generate at least one control signal representative of the detected image; and
- a processing unit configured for the following:
    - receiving, from the detection system, said at least one control signal; and
    - analysing said at least one control signal in order to detect a possible presence of flaws.

29. The apparatus as claimed in claim 28, wherein the deformation system comprises a compression member and an actuator member adapted to move the compression member along the direction of the compression force.

30. The apparatus as claimed in claim 29, wherein the compression member comprises a framework mounted on an end of the actuator member and a cylindrical compression roller mounted on the framework in a manner such that the cylindrical compression roller can freely rotate around an axis thereof.

31. The apparatus as claimed in claim 30, wherein the axis of the compression roller lies on a plane passing through the axis of the tyre and through a radial direction of the lateral wall portion subjected to deformation.

32. The apparatus as claimed in claim 30, wherein a length of the roller along the axis thereof is greater than the radial length of the lateral wall of the tyre.

33. The apparatus as claimed in claim 30, wherein the framework comprises a bracket on which the cylindrical compression roller is mounted rotatably free, the bracket being hinged on a remaining body of the framework in a manner such that the bracket, and the cylindrical compression roller therewith, can oscillate around an oscillation axis, where the oscillation axis is perpendicular to the axis of the tyre and perpendicular to the radial direction of the lateral wall portion subjected to deformation.

34. The apparatus as claimed in claim 33, wherein the oscillation axis, in rest position of the cylindrical compression roller, is placed above, with reference to a vertical direction parallel to the rotation axis of the tyre, a median portion of the cylindrical compression roller.

35. A tyre production line comprising at least one work station, at least one moulding and vulcanisation station, and at least one control station comprising an apparatus for controlling tyres as claimed in claim 28.

36. The production line as claimed in claim 35, wherein the tyre control station comprises a first and a second apparatus for controlling tyres and, interposed between the first and the second apparatus, with reference to a production flow, a tyre overturning machine adapted to arrange the tyre on a support of the second apparatus on a sidewall opposite a sidewall which lies on a support of the first apparatus.

* * * * *